United States Patent
Haupt (10) Patent No.: US 7,645,279 B1
(45) Date of Patent: Jan. 12, 2010

(54) BONE FIXATION METHOD

(76) Inventor: Bruce F. Haupt, 405 Quarry Pointe, Charleston, WV (US) 25301

( * ) Notice: Subject to any disclaimer, the term of this patent is extended or adjusted under 35 U.S.C. 154(b) by 10 days.

(21) Appl. No.: 12/146,662

(22) Filed: Jun. 26, 2008

Related U.S. Application Data (62) Division of application No. 10/891,270, filed on Jul. 14, 2004, now abandoned.

(60) Provisional application No. 60/490,215, filed on Jul. 25, 2003.

(51) Int. Cl.
*A61F 5/04* (2006.01)
*A61F 4/00* (2006.01)
*A61B 17/00* (2006.01)

(52) U.S. Cl. .......................... 606/54; 606/59
(58) Field of Classification Search ............. 606/54–59, 606/300, 301, 302, 313, 328; 411/34, 35, 411/954
See application file for complete search history.

(56) References Cited

U.S. PATENT DOCUMENTS

| | | | |
|---|---|---|---|
| 3,383,975 A * | 5/1968 | Cushman | 411/92 |
| 4,175,555 A | 11/1979 | Herbert | |
| 4,185,624 A * | 1/1980 | Gentile | 606/54 |
| RE31,809 E | 1/1985 | Danieletto et al. | |
| 4,615,338 A | 10/1986 | Ilizarov et al. | |
| 4,653,486 A | 3/1987 | Coker | |
| 4,662,365 A | 5/1987 | Gotzen et al. | |
| 4,760,843 A * | 8/1988 | Fischer et al. | 606/304 |
| 4,828,277 A | 5/1989 | De Bastiani et al. | |
| 4,946,179 A | 8/1990 | De Bastiani et al. | |
| 4,950,270 A | 8/1990 | Bowman et al. | |
| RE33,348 E | 9/1990 | Lower | |
| 4,978,347 A | 12/1990 | Ilizarov | |
| 4,978,348 A | 12/1990 | Ilizarov | |
| 5,019,079 A | 5/1991 | Ross | |

(Continued)

*Primary Examiner*—Thomas C Barrett
*Assistant Examiner*—Andrew Yang
(74) *Attorney, Agent, or Firm*—Keith R. Haupt, Esq.; Wood, Herron & Evans, LLP (57) ABSTRACT

A pin allows for convenient and noninvasive adjustment and tightening relative to the bone to correct and/or avoid loosening of the pin and attached external fixator. In one embodiment, the pin includes a shank extending from a head toward a distal tip end of the pin. Adjacent to the distal tip of the pin is a threaded region with a varying pitch and the shank of the pin is tapered or conical having an increasing minor and/or major diameter along the pin from the tip end. In an alternative embodiment, an anchor is provided on the distal tip for engagement with the far cortex of the bone. The anchor includes a tapered region proximate the tip that decreases in diameter. A split ferrule, expansion bushing or collar is seated on the tapered region. The shank of the pin also includes a threaded region on which a washer and nut are engaged for rotational movement longitudinally on the shank. The pin is initially inserted through a hole in the bone so that the tapered region adjacent the distal tip projects through the distal edge of the bone and the expansion ferrule is seated within the far cortex of the bone. The ferrule advances along the tapered region and expands to securely seat within the far cortex of the bone for anchoring the external fixator. In either embodiment, subsequent to initial pin installation into the bone, if the pin becomes loose relative to the bone, additional rotation of the pin re-establishes a secure pin-bone interface.

20 Claims, 5 Drawing Sheets

U.S. PATENT DOCUMENTS

| | | |
|---|---|---|
| 5,026,374 A | 6/1991 | Dezza et al. |
| 5,062,844 A | 11/1991 | Jamison et al. |
| 5,067,954 A | 11/1991 | Ilizarov |
| 5,167,664 A | 12/1992 | Hodorek |
| 5,281,221 A | 1/1994 | Tadych |
| 5,306,278 A | 4/1994 | Dahl et al. |
| 5,766,179 A | 6/1998 | Faccioli et al. |
| 5,951,556 A | 9/1999 | Faccioli et al. |
| 5,961,515 A | 10/1999 | Taylor et al. |
| 5,971,984 A | 10/1999 | Taylor et al. |
| 6,024,745 A | 2/2000 | Faccioli et al. |
| 6,102,911 A | 8/2000 | Faccioli et al. |
| 6,183,475 B1 | 2/2001 | Lester et al. |
| 6,461,358 B1 | 10/2002 | Faccioli et al. |
| 6,491,694 B1 | 12/2002 | Orsak |
| 6,537,274 B1 | 3/2003 | Katz |
| 6,716,212 B1 | 4/2004 | Pickens |
| 2001/0037113 A1 | 11/2001 | Justin |
| 2003/0187444 A1 | 10/2003 | Overaker et al. |
| 2004/0073221 A1 | 4/2004 | Biscup |
| 2005/0119656 A1 | 6/2005 | Ferrante et al. |

\* cited by examiner

BONE FIXATION METHOD

This is a divisional of U.S. patent application Ser. No. 10/891,270, filed Jul. 14, 2004, which in turn claimed the benefit of U.S. Provisional Patent Application Ser. No. 60/490,215, filed Jul. 25, 2003 and each of these prior applications is hereby incorporated by reference in its entirety.

BACKGROUND OF THE INVENTION

This invention relates generally to an external fixation system for bones, and more specifically, to a pin assembly for use in attachment of the external fixation system to the bones and an associated method of use.

In the practice of medicine, and particularly orthopedic medicine, treatment of certain injuries or conditions is accomplished with a system including an external frame that is attached to the bones with pins or wires. Such systems are commonly referred to as orthopedic external fixators or external skeletal fixators. External fixators are commonly utilized to treat acute fractures of the skeleton, soft tissue injuries, delayed union of the skeleton when bones are slow to heal, non-union of the skeleton when bones have not healed, malunion whereby broken or fractured bones have healed in a mal position, congenital deformities whereby bones develop a mal position, bone infections, bone tumors and bone lengthening, widening or twisting applications. Well known types of external fixators generally include the Ilizarov fixator that is often used for repair of heavily damaged or heavily traumatized bone, the Taylor frame and the limb reconstruction system (LRS).

The use of many external fixators requires multiple pins that are placed through the skin and into the bone. The ends of the pins that stick out from the skin are attached to a rigid framework thereby holding the fractured bone stable so that it can heal.

In many applications, external fixators of this type are preferred over plaster casts because an external fixator can hold the bone fragments much more rigidly than a cast. The advantages of external fixators are that the external frames are quick and easy to apply and provide excellent rigidity and support for specific fractures. If the fracture is open or compound (meaning the skin over the fracture is penetrated) many orthopedic surgeons prefer external fixators because they reliably and securely position the traumatized bone. Examples of external fixators are shown in U.S. Pat. Nos. 5,067,954; 4,978,348; 4,978,347; and 4,615,338 each listing Gavriil Ilizarov as inventor and incorporated herein by reference. Other well known external fixation devices are commercially available from Orthofix Srl of Verona, Italy and Smith & Nephew, Inc. of Memphis, Tenn.

External fixator frames vary considerably in design and capabilities, and may include multiple or single bars, rods or rings and a number of pins or wires connecting the frame to the bony skeleton. The pins or wires may extend completely through the bony skeleton and out each side of the limb or may extend through the bony skeleton and out only one side of the limb. Pins that extend completely through the bony skeleton and out both sides of the limb are commonly referred to as "transfixation pins." Pins, which extend through the bony skeleton and out only one side of the limb are commonly referred to as "half pins."

The exact location and orientation of the wires and pins are determined by the physician according to anatomic and mechanical factors. In the course of treatment with external fixation, the precise placement of the external fixator and the associated pins and wires is critical for the proper positioning and healing of the traumatized bone. Even slight movement or repositioning of the pins and associated external fixator frame may result in misalignment and repositioning of the traumatized bone often requiring corrective measures by the treating physician including removal, replacement or readjustment of the pins and/or external fixator in a subsequent surgical or similar procedure.

While external fixators of this type have proven to be very beneficial in many applications, certain disadvantages associated with external fixators are readily acknowledged. Specifically, infection is a primary concern with the use of such devices. The pins protrude through the muscle, subcutaneous tissue and skin. Because biological tissue does not adhere to the metal pins, a chronic break remains in the skin around the pins. Healthy skin, by its nature, is an effective barrier to bacteria entry. During insertion of the pin this barrier is compromised. Scar tissue formed around a pin or wire during healing lacks the blood vessels normally found in healthy tissue. The lack of blood flow at the pin or wire insertion site hinders systemic antibiotic delivery to the site where bacteria can freely enter the body. As a result, a rather common complication involving external fixators is infection occurring around the pins.

Investigations have shown that some superficial infection occurs in approximately fifty percent of the pins used in external fixators. A single external fixator utilizes numerous pins (about 6-12 pins typically) thereby increasing the opportunity for infection. The severities of the infections range from a superficial skin infection to a deep bone infection, i.e., osteomyelitis. Deep bone infections, however, resulting in loosening of the pin-bone interface necessitating return to the operating room occur more rarely.

In addition to the obvious problems associated with the infection that must be addressed, pin tract infection for external fixators commonly leads to pin loosening and, in some cases, requires premature pin removal and replacement with a return to the operating room for sterile pin insertion. The pins securing the external fixator to the bones work loose in the bone that leads to failure of the device. If the external fixator is removed or additional pins are required, the healing process can be significantly compromised. This significantly undermines the effectiveness of the external fixator for proper bone/soft tissue healing.

In addition to infection, pin loosening can result from a number of factors including pin design and placement, bone necrosis due to surgical trauma during pin insertion, abnormal contact pressure at the pin-bone interface from unfavorable axial loading on the pins due to faulty frame design, or delay in fracture healing.

As a result, an external fixator and associated pin attachment system which avoids the above-described problems associated with loosening and provides consistently reliable and secure attachment of the fixation device to the bone is required even in potentially infectious environments.

SUMMARY OF THE INVENTION

These and other objectives of the invention have been attained by a pin for use with an external fixator and the associated combination and method of use. The pin according to this invention allows for convenient and noninvasive adjustment and tightening of the pin relative to the bone to correct and/or avoid loosening of the pin and attached external fixator. Advantageously, this is readily accomplished without the requirement of adding additional pins to the external fixator or returning to the operating room for removal or replacement of the pins that have become loose as a result of infection or any other cause. Moreover, the pins according to this invention are compatible with standard insertion, installation and adjustment hardware, techniques and procedures for known pin designs. Furthermore, pin designs according to this invention accommodate a variety of coatings that further minimize the likelihood of loosening of the pin relative to the bone. Pin designs according to this invention can be manufactured from a variety of materials that are more compatible with the physical characteristics of the bone structure, external fixator and other criteria, including the modulus of elasticity of the bone being repaired.

In certain embodiments of this invention, the pin is a half pin that extends into the proximal bone cortex through the muscles and skin to the outside of the body for attachment to the external fixator. In one embodiment, the pin according to this invention includes a head for securely mounting to the external fixator and a shank extending from the head toward a distal tip end of the pin. Adjacent to the distal tip of the pin in one embodiment is a threaded region in which the shank of the pin is tapered or conical having an increasing minor and/or major diameter along the pin from the tip end. Moreover, the threaded region of the pin includes a varying pitch thread such that the spacing between adjacent threads increases. Therefore, subsequent to initial pin installation into the bone and attachment of the external fixator, if the pin becomes loose relative to the bone, additional rotation of the pin advances the insertion of the pin into the bone and the increasing pitch of the threads and the conical shape of the pin increases the grip of the pin in the bone to re-establish a secure pin-bone interface. As the pin is inserted further into the bone, the threads engage portions of the bone that are not infected or worn as a result of movement of the pin in the bone. Advantageously, the distal tip of the pin according to one embodiment includes a self-tapping flute to assist in the insertion into the bone and advancement of the pin therein.

In an alternative embodiment of the pin according to this invention, an anchor is provided on the distal tip for engagement with the far cortex of the bone. In one form according to this invention, the anchor includes a tapered region proximate the tip that decreases in diameter. A split ferrule, expansion bushing or collar is seated on the tapered region adjacent a bulk head on the shank of the pin. The shank of the pin also includes a threaded region on which a washer and nut are threadably mounted for movement longitudinally on the shank. The pin is initially inserted through a hole in the bone so that the tapered region adjacent the distal tip projects through the distal edge of the bone and the expansion ferrule is seated within the far cortex of the bone. The washer and nut combination are seated on the proximal surface of the near cortex of the bone and rotation of the nut relative to the pin retracts the pin relative to the bone and expands the ferrule. The ferrule advances along the tapered region and expands to securely seat within the far cortex of the bone for anchoring the external fixator.

Subsequently, if the pin becomes loose relative to the bone as a result of an infection or other factors, an adjustment of the pin through rotation relative to the nut further retracts the pin and expands the ferrule to re-establish a secure pin-bone interface in the far cortex of the bone. Advantageously, the anchor according to this invention provides for secure initial installation of the pin and reliable, non-invasive adjustment of the pin for a continued stable pin-bone interface and positioning of the external fixator throughout the healing process.

In any embodiment according to this invention, a cannula may be provided through the longitudinal centerline of the pin to assist in the initial positioning and placement thereof. Additionally, pins according to this invention may be advantageously manufactured from materials that are consistent with the physical properties of the bone and associated external fixator. Specifically, the pin may be manufactured from not only stainless steel, but also titanium, nitonol, ceramics, bioabsorbables, carbon fiber composites and the like. These materials provide for more strength, less weight and a more comparable modulus of elasticity with respect to the bone structure to provide a more natural and consistent flexure of the pin-bone union to assist in healing of the traumatized bone. Moreover, the pin material may be coated with hydroxyapatite or an antibiotic as is well known.

Therefore, as a result of a pin according to this invention and associated external fixators, reliable and secure attachment of the fixator is provided throughout the entire length of the installation of the fixator. Pin loosening as a result of infection or other sources is avoided through noninvasive and easily accomplished adjustment of the pin to maintain secure and stable positioning of the fixator and attached bone structure without resort to the operating room, additional pin installation or other drastic treatment options.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

DETAILED DESCRIPTION OF THE INVENTION

Figure 1:
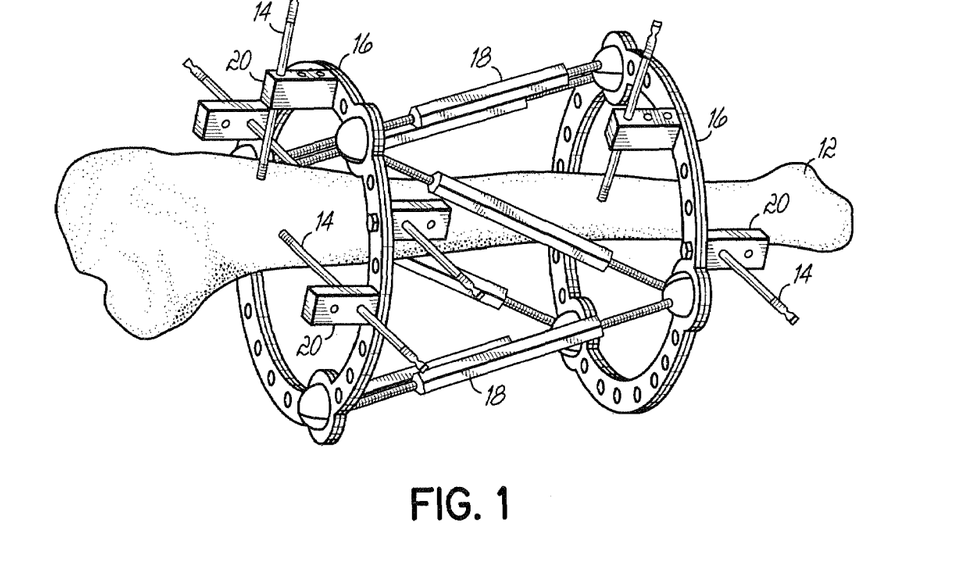
FIG. 1 is a perspective view of an exemplary external fixator mounted to a bone with a pin according to one embodiment of this invention.

Referring to FIG. 1, an exemplary fixator 10 mounted to a bone 12 via pins 14 according to this invention is shown. The external fixator 10 is used in orthopedic surgery for stabilizing fractured bones 12. However, it should be understood that the invention is not limited to use with any specific external fixator design or associated device. The pin 14 of this invention is readily employed in other bone, spine, or other applications with or without a fixator 10.

External fixators 10 can be used as an external skeletal fixation system to secure or affix a first bone element relative to a second bone element in the event of a break, trauma, fracture, nonunion, malunion or the like. As shown in FIG. 1, the external fixator 10 may include a pair of rings 16 surrounding the bone 12. The rings 16 are connected together by adjustable struts 18. Examples of representative external fixators which are compatible with this invention are disclosed in U.S. Pat. Nos. 5,961,515; 4,978,348; 4,978,347; 4,615,338; 5,062,844; 4,662,365; 5,951,556; 6,102,911; 6,461,358; 6,491,694; and 5,971,984, each of which is hereby incorporated by reference in its entirety.

The rings 16 and/or adjustable struts 18 as well as other components in combination provide an external fixator frame adapted to be mounted to the bone 12 by a number of pins 14. The pins 14 are coupled to clamp blocks 20 mounted on the rings 16. The word "pin" is used herein to encompass standard transfixation pins, half pins, wires, screws, bolts, spine implants and the like.

As shown particularly in FIGS. 1, 4-6 and 8-9, the pins 14 of this invention are intended to be coupled to the external fixator 10 frame and inserted into the bone 12. Generally, the bone 12 includes a near cortex 22 and a far cortex 24 spaced therefrom. Between the near and far cortex portions 22, 24 of the bone 12 is a cancellous bone region 26. While the bone 12 shown and generally described herein is referred to as a cortical bone that makes up most of the long bones in the arms and legs, this invention is readily used with both cortical and spongy (cancellous) bone structures. Additional applications for this invention include use as a rotator cuff anchor in the proximal humerus or soft tissue anterior cruciate ligament (ACL) reconstruction of the knee.

Despite substantial improvement in metallurgy, design and understanding of the biomechanical forces acting on the fixator frame 10, the pin-bone interface has remained a major site of complications leading to treatment failure in known fixator and pin-bone interface connections. The pin-bone interface is the most critical component of the fixator system. The biomechanical factors that influence the "rigidity" of an external fixation frame include the pin diameter, pin design, location of the pins in relation to the bone fracture site, as well as to each other, the location of the connecting bar/strut and its distance from the underlying bone, the degree of osseous contact, which influences how much of a physiological load would be borne by either the fixator frame alone or by the bone and frame together. Pin loosening can result from a number of factors including pin design and placement, bone necrosis due to surgical trauma during pin insertion, abnormal contact pressure at the pin-bone interface from unfavorable loading on the pins due to faulty frame design, or delay in fracture healing.

Figure 2:
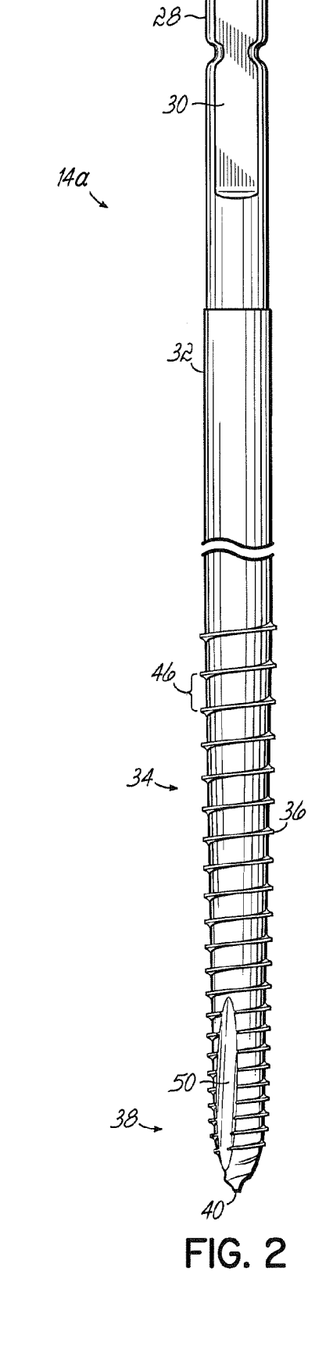
FIGS. 2 and 3 are plan views of first and second alternative embodiments of the pin for use with the external fixator according to this invention.
Figure 3:
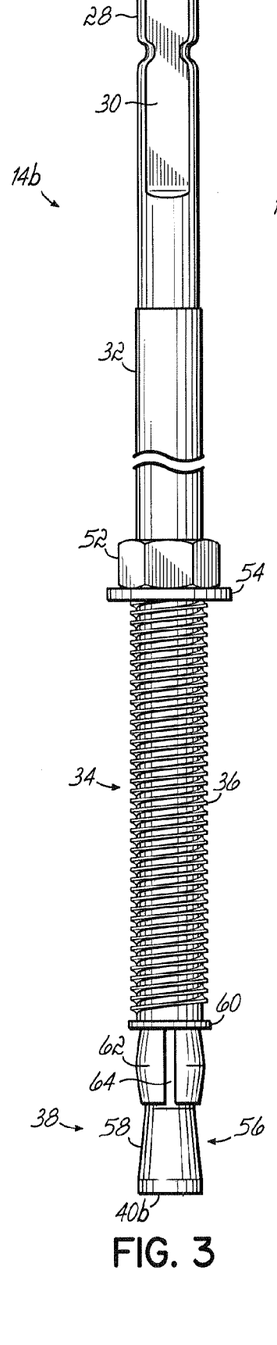
Figure 4:
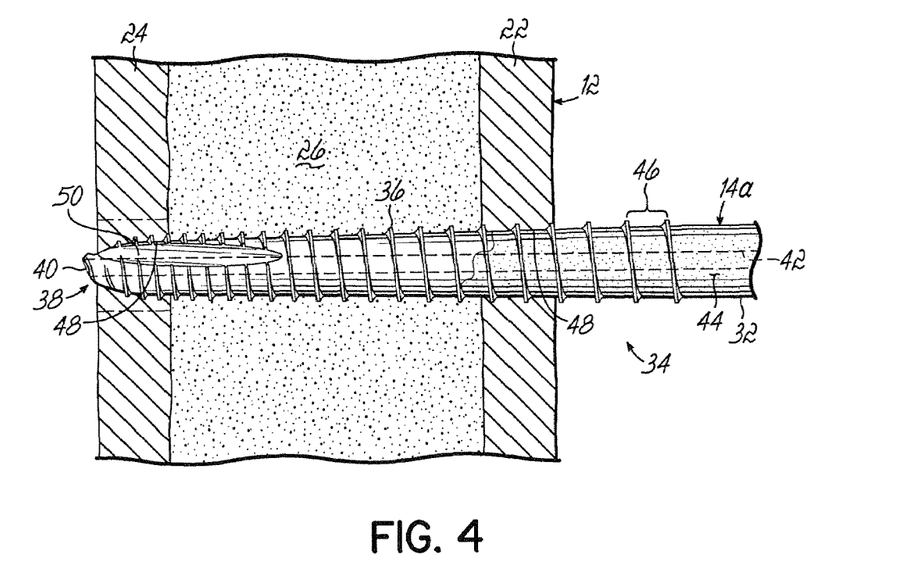
FIG. 4 is a cross-sectional view of a bone with the pin of FIG. 2 inserted therein for mounting the external fixator.
Figure 7:
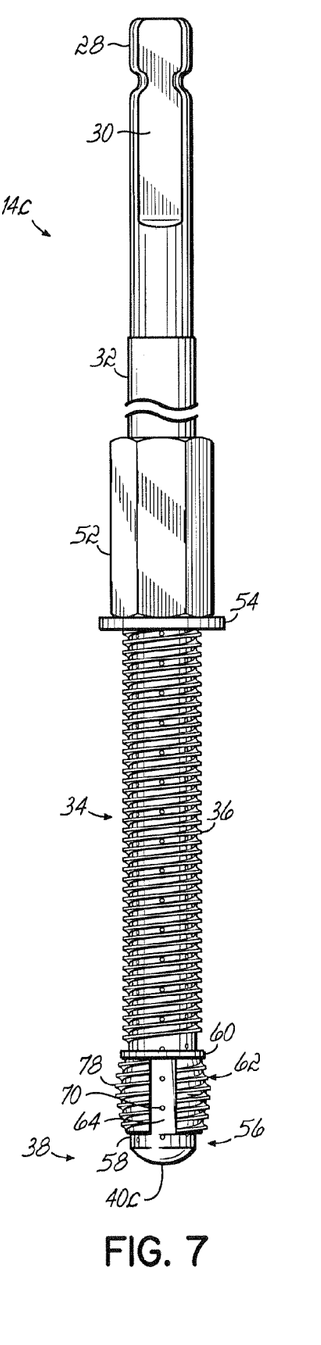
FIG. 7 is a plan view a third alternative embodiment of the pin for use with the external fixator according to this invention.

Three embodiments of the pin 14 according to this invention are shown in FIGS. 2, 3 and 7. Each pin 14a, 14b, 14c in FIGS. 2, 3 and 7, respectively, includes a head end 28 with an operational configuration such as a D flat 30 or other configuration for mating compatibility with drills or the like commonly found in operating rooms such as an AO Quick Connect for convenient and ready attachment to a drill, powered operator (not shown) or the like. Each pin 14a, 14b, 14c likewise includes an elongated shank 32 having a threaded region 34 with a helical thread 36 projecting from the shank 32 and a terminal region 38 including a tip 40 of the pin 14.

Preferably, the pins 14a, 14b, 14c according to this invention as shown in FIGS. 4-6 and 8-9 each include a longitudinal, centrally positioned cannula 42. A cannula passage 42 in the pin 14 assists in proper alignment and initial positioning and insertion of the pin 14 through an established technique. Additionally, the cannula 42 of any embodiment of the pin 14 is in communication with each of a number of fenestrations 70, as shown in pin 14c of FIG. 7, extending at least a portion of the length of the shank 32 of the pin 14c for convenient delivery of fluids or gases to the bone 12 and/or surrounding tissues. This can be very beneficial for treatment of infections through the delivery of antibiotics or other medications in either a hospital, operating room, out patient facility or doctor's office environment.

Preferably each pin 14 according to this invention includes a hydroxyapatite (HA) or antibiotic coating 44 to aid in a secure pin-bone interface. The HA coating 44 may extend a substantial portion of the length of the pin 14, including the threaded region 34 as well as other regions of the pin 14. Moreover, the pin 14 according to this invention is preferably manufactured from steel, stainless steel and more preferably from titanium, nitonol, ceramic, bioabsorbable or composite (carbon fiber) materials. Most preferably, the pin material has a modulus of elasticity closely matching that of the modulus of elasticity of bone to provide a more natural flex and consistent reaction to stress and movement between the bone 12 and pin 14 materials.

In a first embodiment of the pin 14a shown in FIG. 2, the threaded region 34 of the pin 14a is tapered or conical such that a minor diameter of the shank 32 decreases along the shank 32 toward the tip 40 of the pin 14a. The major diameter of the thread 36 on the shank 32 may likewise decrease toward the tip 40. Advantageously, the pitch or spacing 46 between adjacent portions of the helical thread 36 on the pin 14a of FIG. 2 increases from the tip 40 toward the head end 28. The pitch 46 increases in the threaded region 34 to provide for a secure and stable attachment of the pin 14a to the bone 12.

The increasing pitch and conical tapered shape of the threaded region 34 of the pin 14a in FIG. 2 advantageously overcomes many of the sources of pin 14a loosening. After initial insertion of the pins 14a in the bone, periodic adjustment of the pins 14a is available without returning to the operating room for additional procedures or more invasive office/out-patient procedures. Rotation of the pin 14a relative to the bone 12 to further insert the pin 14a into the bone 12 corrects any loosening that may have occurred after initial insertion. The pin 14a may loosen within the original hole 48 (FIG. 4) in the bone 12 and continued rotation and adjustment of the pin 14a will advance the pin 14a in the hole 48 thereby increasing the diameter of the hole 48 in each portion of the bone 12 and consequently re-establishing a secure pin-bone interface and secure attachment of the fixator 10. The increased pitch 46 of the thread 36 alone or in combination with the conical, tapered configuration of the pin 14a allows the pin 14a to achieve increased holding power and overcome potential infected regions IF (FIGS. 4 & 5) of the bone that may have resulted in pin 14 loosening. Removal of the pin 14a of FIG. 2 is easily accomplished by reverse rotation of the pin 14a for retraction out of the bone 12.

The pin 14a of FIG. 2 also includes a self-tapping flute 50 proximate the tip end 40 for easier initial insertion into the bone 12. The self-tapping flute 50 provides the advantage that predrilling a hole in the bone 12 for insertion of the pin 14a is not required.

Referring to FIG. 3, an alternative embodiment of the pin 14 according to this invention is shown. The pin 14b includes the head end 28 as well as the threaded region 34. The threaded region 34 of the pin 14b has a generally constant diameter and constant pitch for the helical thread 36. The threaded region 34 is compatible with internal threads on a nut 52 and washer 54 combination that may be separate pieces or welded together. Adjacent the terminal tip 40b of the pin 14b according to this embodiment is an anchor 56. In one embodiment, the anchor 56 includes a blunt tip 40b and a tapered region 58 extending from the blunt tip 40b. The tapered region 58 has a larger circumference and diameter adjacent the blunt tip 40b, each of which decreases axially toward a circumferentially extending bulkhead 60. A split ferrule, bushing or collar 62 which may be constructed of a more ductile material than the pin 14b for ease of expansion/contraction is mounted circumferentially around the pin 14b on the tapered region 58. The ferrule 62 is split circumferentially and includes a gap 64.

Figure 5:
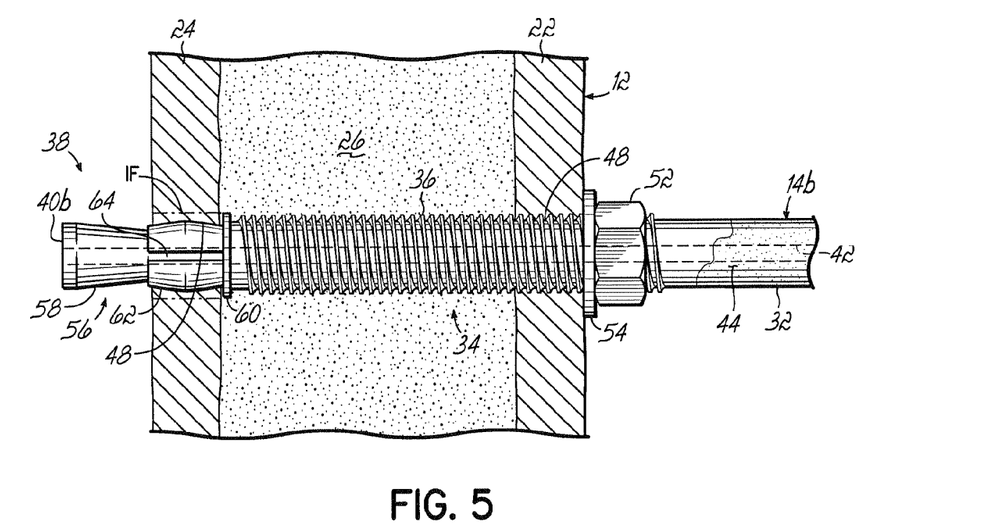
FIG. 5 is a view similar to FIG. 4 of the pin shown in FIG. 3.
Figure 6:
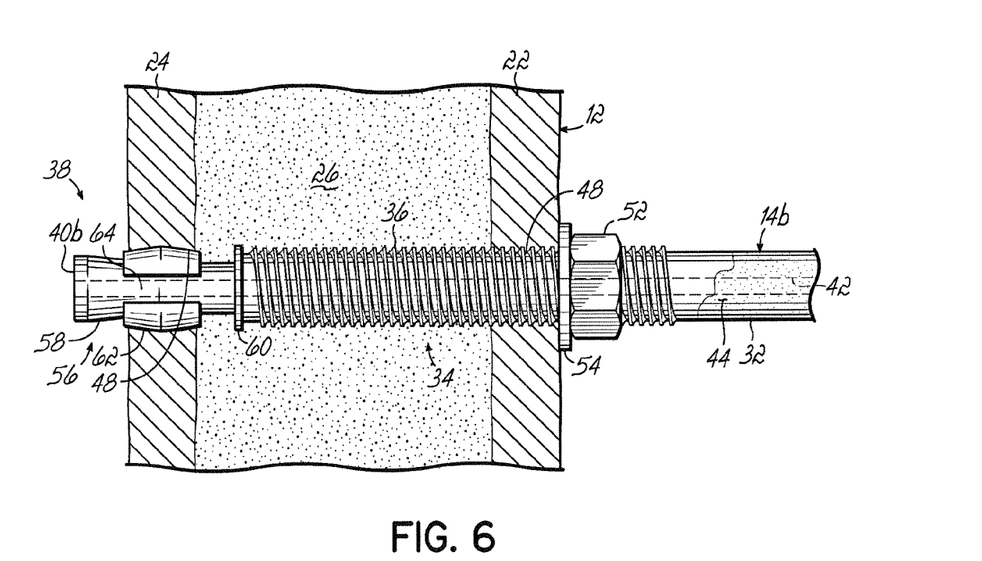
FIG. 6 is a view similar to FIG. 5 with the pin adjusted to overcome loosening of the pin relative to the bone.

The pin 14b of FIG. 3 is initially inserted after the skin (not shown) is incised and the subcutaneous tissue, deep fascia and muscle are dissected to the bone 12. Preferably, the bone 12 is drilled and tapped so that a hole 48 is drilled into the near and far cortex 22, 24 and cancellous regions 26 of the bone 12. The blunt tip 40b and anchor 56 of the pin 14b are then inserted together to the target depth in either cortical or cancellous bone until the ferrule 62 is deployed at the target depth. Likewise, the washer and nut 54, 52 combination are juxtaposed to the proximal surface of the near cortex 22 of the bone 12 as shown in FIG. 5. The nut 52 is then rotated relative to the threaded region 34 of the pin 14b to initially retract the shank 32 of the pin 14b relative to the bone 12. Rotation of the nut 52 relative to the shank 32 to advance the nut 52 toward the blunt tip 40b end of the pin 14b retracts the pin 14b and thereby moves the tapered region 58 of the pin 14b relative to the ferrule 62 seated in the far cortex 24 of the bone 12. As a result, the ferrule 62 advances slightly on the tapered increasing diameter region 58 and the diameter and circumference of the ferrule 62 and size of the gap 64 likewise increases to securely seat the ferrule 62 and pin 14b within the far cortex 24 of the bone 12. As such, the pin 14b is securely anchored in the bone 12 for attachment of the external fixator 10. The most common loosening mechanism is infection at the pin-bone interface.

However, loosening may occur as is common in many situations. The region of the far cortex 24 proximate the ferrule 62 may become infected is indicated by region IF of FIG. 5 thereby loosening the pin-bone interface. In addition to treating the infection, the pin-bone interface loosening presents a significant problem to the stability of the fixator 10 and ultimate success of the bone union because the infected region IF affords a less severe interface with the pin 14.

Advantageously, according to this invention, the pin-bone interface is re-secured by additional rotation of the pin 14b relative to the nut 52 thereby further advancing the ferrule 62 seated within the far cortex 24 relative to the blunt tip 40b and increasing the diameter and circumference of the ferrule 62 to engage unaffected regions of the cortex 24 for a secure pin-bone interface. One major advantage of the blunt design of the tip 40b is minimal risk to neurovascular structures past the bone cortex 24. Throughout the use of the external fixator 10, adjustment of the pin 14b through rotation of the nut 52 relative to the threaded region may be required to maintain secure fixation. Comparison between FIGS. 5 and 6 of the position of the ferrule 62 on the tapered region 58, size of the gap 64 and position of the nut 52 on the threaded region 34 demonstrates the adjustment.

Removal of the pin 14b is easily accomplished through reverse rotation of the pin 14b relative to the nut 52 to advance the nut 52 toward the head end 28 thereby initially projecting the blunt tip 40b further into the body relaxing stress on the ferrule 62 for disengagement with the far cortex 24 and removal of the pin 14b. Advantageously, the anchor 56 which securely engages the far cortex 24 provides a stable pin-bone interface without trauma or damage to blood vessels, nerves or other soft tissue adjacent the bone 12 and particularly at the far side of the far cortex 24. The tip 40b of the pin 14b is blunt and thereby less likely to pierce, puncture or otherwise damage bodily components adjacent the bone 12 into which the anchor 56 is engaged. As such, the pin 14b of this invention is not only uniquely suited for use in external fixator applications but also spine or vertebrae related applications in which insertion of prior art pins or screws potentially damages the aorta and/or other bodily vessels or components proximate the spine.

Referring to FIG. 7, a further alternative embodiment of the pin 14 according to this invention is shown. The pin 14c includes the head end 28 as well as the threaded region 34. The threaded region 34 of the pin 14c has a generally constant diameter and constant pitch for the helical thread 36. The threaded region 34 is compatible with internal threads on a nut 52 and washer 54 combination that are preferably welded or otherwise united together. Preferably, the length of the nut 52 extends from the near cortex 22 of the bone 12 and through a muscle layer 72, a region of fat 74 and the epidermis or skin layer 76 to be exposed outside of the body for access by the doctor or clinician for adjustment and manipulation as required.

Adjacent the terminal tip 40c of the pin 14c according to this embodiment is an anchor 56. In one embodiment, the anchor 56 includes a dome shaped, hemispherical tip 40c and a tapered region 58 extending from the tip 40c. The tapered region 58 has a larger circumference and diameter adjacent the tip 40c, each of which decreases axially toward a circumferentially extending bulk head 60. A split ferrule, bushing or collar 62 which may be constructed of a more ductile material than the pin 14c for ease of expansion/contraction is mounted circumferentially around the pin 14c on the tapered region 58. The ferrule 62 is split circumferentially and includes a gap 64. The ferrule 62 may include serrations or threads 78 on the outer surface thereof to aid in engaging the cortex 24 of the bone 12. Moreover, the tip 40c of the pin 14c is preferably integral with the tapered region 58. Preferably, the ferrule 62 is mounted for free rotation relative to the tapered region 58 prior to engagement with the bone 12.

Figure 8:
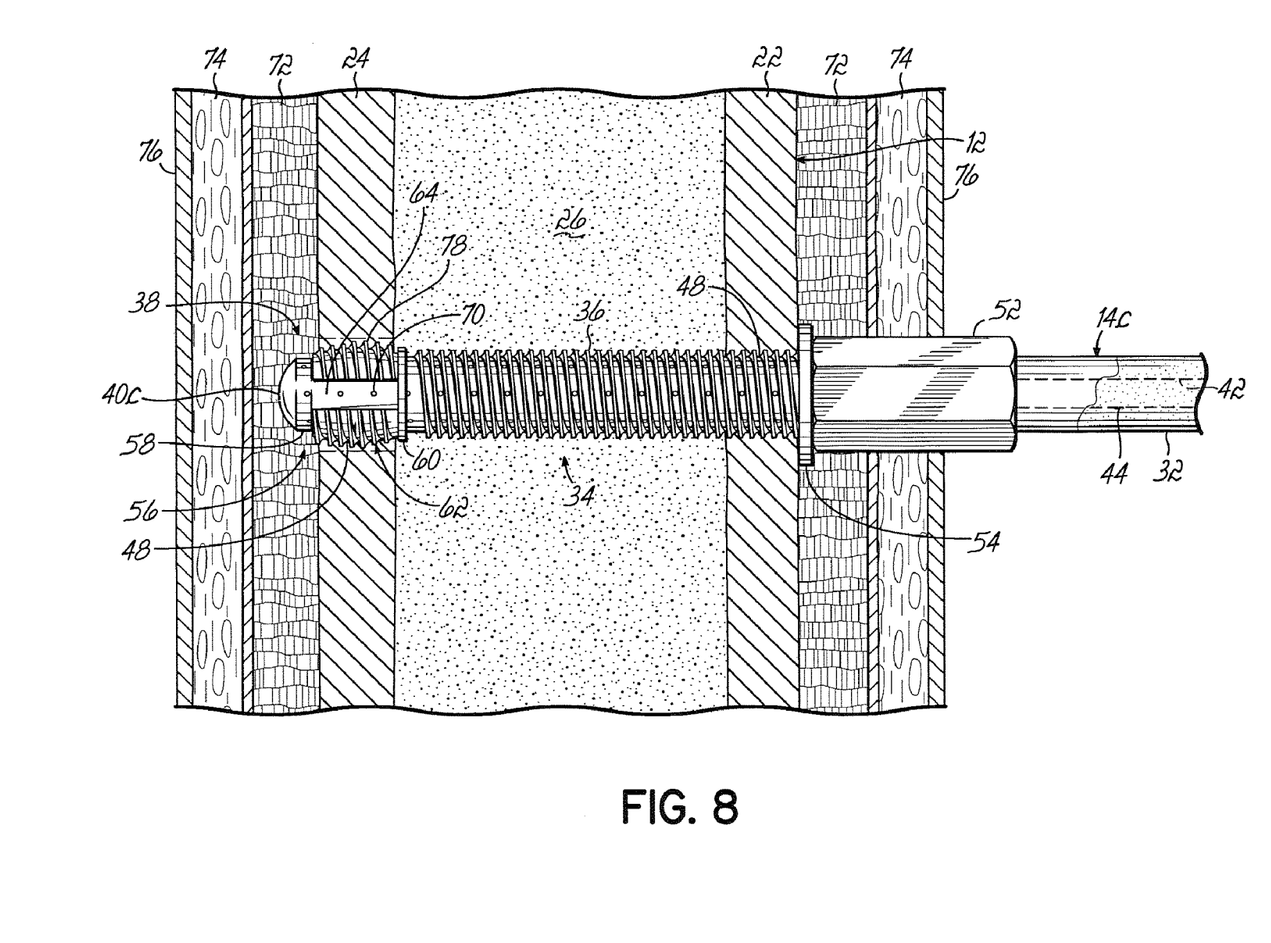
FIG. 8 is a cross-sectional view of a bone, surrounding tissue and associated bodily components with the pin of FIG. 7 inserted therein before deployment and tightening for mounting the external fixator frame.

The pin 14C of FIG. 7 is initially inserted after the skin 76 is incised and the subcutaneous tissue, deep fascia and muscle 72 are dissected to the bone 12. Preferably, the bone 12 is drilled and tapped so that a hole 48 is drilled into the near and far cortex 22, 24 and cancellous regions 26 of the bone 12. The blunt tip 40c and anchor 56 of the pin 14c are then inserted together to the target depth in either cortical or cancellous bone until the ferrule 62 is deployed at the target depth. Likewise, the washer and nut 54, 52 combination are juxtaposed to the proximal surface of the near cortex 22 of the bone 12 as shown in FIG. 8. The nut 52 is then rotated relative to the threaded region 34 of the pin 14c to initially retract the shank 32 of the pin 14c relative to the bone 12. Rotation of the nut 52 relative to the shank 32 to advance the nut 52 toward the blunt tip 40c end of the pin 14c retracts the pin 14c and thereby moves the tapered region 58 of the pin 14c relative to the ferrule 62 seated in the far cortex 24 of the bone 12. As a result, the ferrule 62 advances slightly on the tapered increasing diameter region 58 and the diameter and circumference of the ferrule 62 and size of the gap 64 likewise increases to securely seat the ferrule 62 and pin 14c within an expansion/contraction region of the far cortex 24 of the bone 12 adjacent to the ferrule 62. As such, the pin 14c is securely anchored in the bone 12 for attachment of the external fixator 10.

However, loosening may occur as is common in many situations. The most common loosening mechanism is infection at the pin-bone interface. The region of the far cortex 24 proximate the ferrule 62 may become infected is indicated by region IF of FIG. 9 thereby loosening the pin-bone interface. In addition to treating the infection via the administration of antibiotics through the fenestrations 70, the pin-bone interface loosening presents a significant problem to the stability of the fixator 10 and ultimate success of the bone union because the infected region IF affords a less severe interface with the pin 14.

Figure 9:
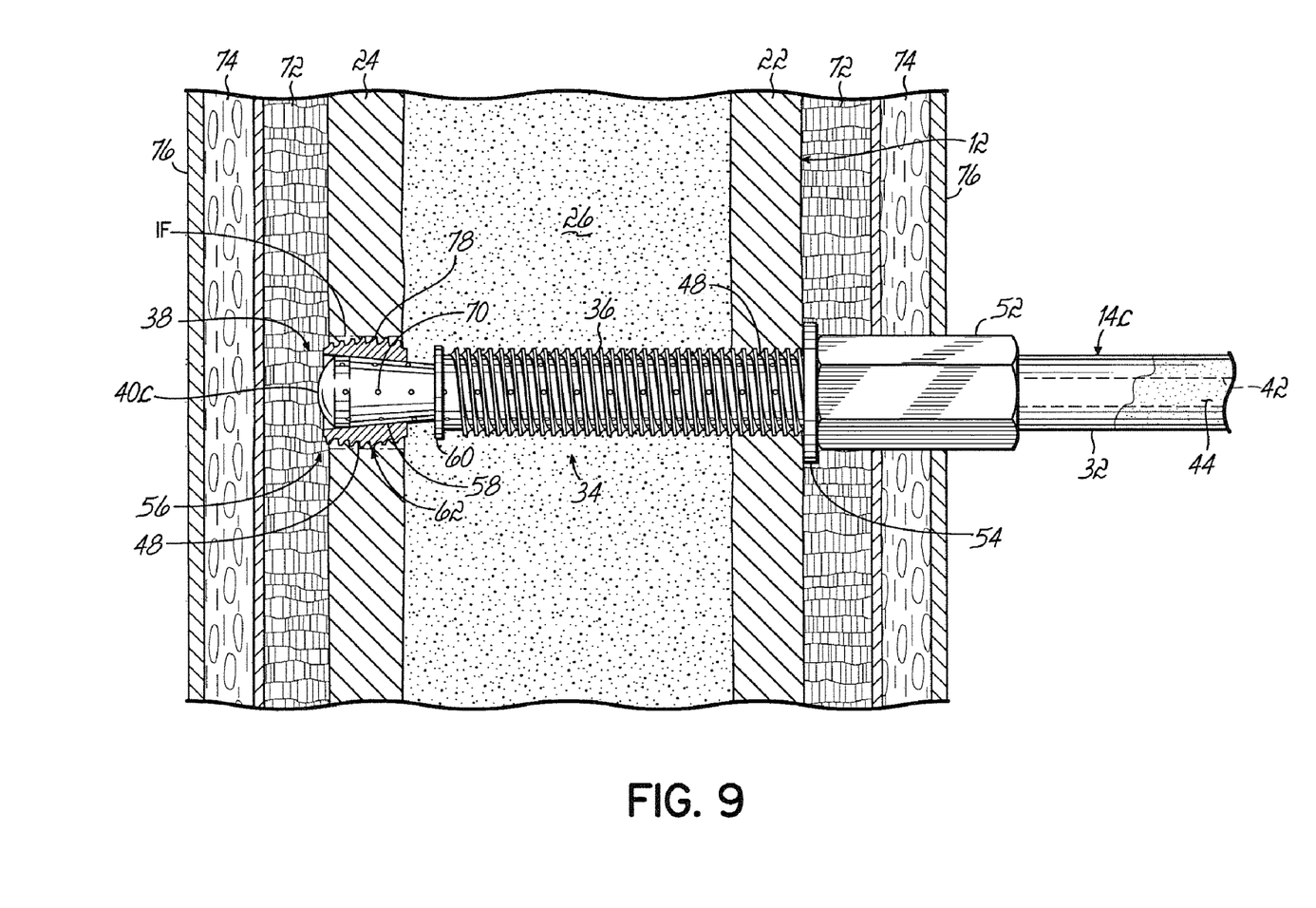
FIG. 9 is a view similar to FIG. 8 with the pin securely deployed in the bone for mounting the external fixator frame.

Advantageously, according to this invention, the pin-bone interface is re-secured by additional rotation of the pin 14c relative to the nut 52 thereby further advancing the ferrule 62 seated within the far cortex 24 relative to the blunt tip 40c and increasing the diameter and circumference of the ferrule 62 to engage unaffected regions of the cortex 24 for a secure pin-bone interface.

One major advantage of the design of the tip 40c is minimal risk to neurovascular structures past the bone cortex 24. The dome shaped configuration of the tip 40c upon initial installation of the pin 14c creates a safe zone adjacent the far cortex 24 proximate the pin 14c. The dome shaped tip 40c pushes away any veins, nerves, arteries or other bodily components that might otherwise be damaged by pins or other devices inserted into the bone 12.

Throughout the use of the external fixator 10, adjustment of the pin 14c through rotation of the nut 52 relative to the threaded region may be required to maintain secure fixation. Comparison between FIGS. 8 and 9 of the position of the ferrule 62 on the tapered region 58, size of the gap 64 and position of the nut 52 on the threaded region 34 demonstrates the adjustment.

Removal of the pin 14C is easily accomplished through reverse rotation of the pin 14C relative to the nut 52 to advance the nut 52 toward the head end 28 thereby initially projecting the blunt tip 40c further into the body relaxing stress on the ferrule 62 for disengagement with the far cortex 24 and removal of the pin 14c. Advantageously, the anchor 56 which securely engages the far cortex 24 provides a stable pin-bone interface without trauma or damage to blood vessels, nerves or other soft tissue adjacent the bone 12 and particularly at the far side of the far cortex 24. The tip 40c of the pin 14c is blunt and thereby less likely to pierce, puncture or otherwise damage bodily components adjacent the bone 12 into which the anchor 56 is engaged. As such, the pin 14c of this invention is not only uniquely suited for use in external fixator applications but also spine or vertebrae related applications in which insertion of prior art pins or screws potentially damages the aorta and/or other bodily vessels or components proximate the spine.

From the above disclosure of the general principles of the present invention and the preceding detailed description of at least one preferred embodiment, those skilled in the art will readily comprehend the various modifications to which this invention is susceptible. Therefore, we desire to be limited only by the scope of the following claims and equivalents thereof.

I claim:

1. A method for establishing a connection between a pin and a bone, the method comprising the steps of:
    inserting a pin into a bone such that an anchor coupled to the pin proximate a distal tip region of the pin is seated in the bone without the anchor threadably engaging the bone;
    adjusting the pin and anchor to establish a secure interface between the anchor and the bone without the anchor threadably engaging the bone;
    wherein after the pin and anchor have been in the bone and the interface between the anchor and the bone has loosened, then
    further adjusting the pin and anchor to re-establish a secure interface between the anchor and the bone without the anchor threadably engaging the bone; and
    wherein the further adjusting step further comprises, at least in part, radially expanding a portion of the anchor in a direction generally perpendicular to a longitudinal axis of the pin to re-establish the secure interface with the bone.

2. The method of claim 1 further comprising:
    drilling a hole in the bone prior to the inserting step, the hole being adapted to receive the pin therein and extending through both near and far cortex regions and cancellous regions of the bone.

3. The method of claim 2 wherein the anchor is seated in the far cortex region of the bone.

4. The method of claim 1 wherein the adjusting and further adjusting steps each further comprise:
    moving the pin longitudinally relative to the anchor without rotating the pin.

5. The method of claim 4 wherein the pin is moved relative to the anchor so that the anchor is positioned closer to the distal tip of the pin.

6. The method of claim 4 wherein the moving step further comprises:
    rotating a nut threadably engaged on a threaded region of the pin relative to the pin without rotating the pin.

7. The method of claim 1 wherein the further adjusting step further comprises:
    translating the anchor relative to the pin without rotating the pin so that the anchor advances toward a larger diameter portion of a tapered region on the pin to thereby expand radially and re-establish the secure interface with the bone.

8. The method of claim 7 further comprising:
    expanding a gap in a split ferrule member of the anchor to thereby radially expand the split ferrule member as it advances toward the larger diameter portion of the tapered region of the pin.

9. The method of claim 1 further comprising:
    allowing the secure interface between the bone and the anchor to loosen between the adjusting and further adjusting steps.

10. The method of claim 9 further comprising:
    repeating the allowing and the further adjusting steps.

11. The method of claim 1 further comprising:
    removing the pin and anchor from the bone.

12. A method for establishing a connection between a pin and a bone, the method comprising the steps of:
    drilling a hole in a bone, the hole being adapted to receive a pin therein and extending through both near and far cortex regions and cancellous regions of the bone;
    inserting the pin into the hole in the bone such that an anchor coupled to the pin proximate a distal tip region of the pin is seated in the far cortex region of the bone without the anchor threadably engaging the far cortex region of the bone;
    adjusting the pin and anchor to establish a secure interface between the anchor and the bone without the anchor threadably engaging the bone and without rotating the pin;
    allowing the secure interface between the bone and the anchor to loosen;
    further adjusting the pin and anchor to re-establish a secure interface between the anchor and the bone without the anchor threadably engaging the bone and without rotating the pin; and
    wherein the adjusting and the further adjusting steps each further comprises, at least in part, (a) radially expanding a portion of the anchor in a direction generally perpendicular to a longitudinal axis of the pin to establish the secure interface with the bone;
(b) translating the anchor relative to the pin so that the anchor advances toward a larger diameter portion of a tapered region on the pin to thereby expand radially and establish the secure interface with the bone;
(c) expanding a gap in a split ferrule member of the anchor to thereby radially expand the split ferrule member as it advances toward the larger diameter portion of the tapered region of the pin; and
removing the pin and anchor from the bone.

13. The method of claim 12 wherein the adjusting and the further adjusting steps each further comprises:
moving the pin longitudinally relative to the anchor without rotating the anchor.

14. The method of claim 13 wherein the pin is moved relative to the anchor so that the anchor is positioned closer to the distal tip of the pin.

15. The method of claim 14 wherein the moving step further comprises:
rotating a nut threadably engaged on a threaded region of the pin.

16. The method of claim 15 further comprising:
repeating the allowing and the further adjusting steps.

17. A method of installing an external fixation system to a compromised bone, the method comprising the steps of:
installing a plurality of pins at least partially in the bone;
coupling a frame of an external fixator to each of the pins;
wherein the installing step for each of the pins further comprises:
(a) inserting the pin into the bone such that an anchor coupled to the pin proximate a distal tip region of the pin is seated in the bone without the anchor threadably engaging the bone;
(b) adjusting the pin and anchor to establish a secure interface between the anchor and the bone without the anchor threadably engaging the bone;
wherein after the pin and anchor have been in the bone and the interface between the anchor and the bone has loosened, then
(c) further adjusting the pin and anchor to re-establish a secure interface between the anchor and the bone without the anchor threadably engaging the bone and without rotating the pin; and
wherein the further adjusting step further comprises, at least in part, radially expanding a portion of the anchor in a direction generally perpendicular to a longitudinal axis of the pin to re-establish the secure interface with the bone.

18. The method of claim 17 wherein the installing step for each pin further comprises:
drilling a hole in the bone prior to the inserting step, the hole being adapted to receive the pin therein and extending through both near and far cortex regions and cancellous regions of the bone; and
seating the anchor in the far cortex region of the bone without threadably engaging the bone with the anchor.

19. The method of claim 17 wherein the installing step for each pin further comprises:
translating the anchor relative to the pin so that the anchor advances toward a larger diameter portion of a tapered region on the pin to thereby expand radially and re-establish the secure interface with the bone without rotating the pin; and
expanding a gap in a split ferrule member of the anchor to thereby radially expand the split ferrule member as it advances toward the larger diameter portion of the tapered region of the pin without rotating the pin.

20. The method of claim 1 further comprising:
allowing the secure interface between the bone and the anchor of selected pins to loosen between the adjusting and further adjusting steps.

* * * * *